United States Patent [19]
Barnhart et al.

[11] Patent Number: 5,912,391
[45] Date of Patent: Jun. 15, 1999

[54] METHOD FOR HYDROXYLATING AROMATIC COMPOUNDS

[75] Inventors: Terence Michael Barnhart, Schenectady, N.Y.; Annah Waswa Hughes, Ottawa, Canada

[73] Assignee: General Electric Company, Schenectady, N.Y.

[21] Appl. No.: 08/971,777

[22] Filed: Nov. 17, 1997

[51] Int. Cl.$^6$ .................................................... C07C 37/60
[52] U.S. Cl. ............................................................ 568/802
[58] Field of Search ..................... 568/801, 802

[56] References Cited

U.S. PATENT DOCUMENTS

| | | | |
|---|---|---|---|
| 4,338,471 | 7/1982 | Umemura et al. | 568/802 |
| 4,937,376 | 6/1990 | Fields et al. | 562/16 |
| 5,426,245 | 6/1995 | Hamada et al. | 568/802 |

OTHER PUBLICATIONS

Mimoun et al., "Vanadium(V) Peroxo Complexes. New Versatile Biomimetic Reagents for Epoxidation of Olefins and Hydroxylation of Alkanes and Aromatic Hydrocarbons", J. Am. Chem. Soc., 105, 3101–3110 (1983).

CEH Product Review, "Hydrogen Peroxide", SRI Internantional (1996).

*Primary Examiner*—James H. Reamer
*Attorney, Agent, or Firm*—Noreen C. Johnson; Douglas E. Stoner

[57] ABSTRACT

Aromatic compounds such as benzene, toluene and xylene are hydroxylated by reaction with oxygen and hydroquinone or a substituted hydroquinone in the presence of a vanadium compound, typically a pentavalent vanadium oxy chelate with picolinic acid or a substituted picolinic acid. The vanadium compound may be produced in situ by reaction of the chelating agent with a tetravalent or pentavalent precursor vanadium compound.

22 Claims, No Drawings

METHOD FOR HYDROXYLATING AROMATIC COMPOUNDS

BACKGROUND OF THE INVENTION

This invention relates to the hydroxylation of aromatic compounds by oxidation.

The conversion of aromatic compounds, particularly aromatic hydrocarbons, to their hydroxylated derivatives is of interest as a process with commercial potential since many aromatic compounds suitable as precursors are readily and cheaply available from petrochemical feed stocks. Their conversion to hydroxyaromatic compounds such as phenol by hydroxylation would be advantageous since the products are useful for many purposes, including, in the case of phenol, the synthesis of bisphenol A or 2,2-bis(4-hydroxyphenyl) propane by reaction with acetone. m-Xylene could be similarly converted to 2,6-xylenol, an essential intermediate for the production of the engineering thermoplastic poly(2,6-dimethyl-1,4-phenylene ether). Trimethylbenzenes could be converted to various hydroxy compounds useful as intermediates for such compounds as vitamin E.

A principal obstacle to commercial use of such processes has been the need to synthesize large amounts of metal-containing oxidants for use in hydroxylation. It is known that oxidative hydroxylation may be accomplished with the use of various vanadium peroxo compounds. Reference is made, for example, to Mimoun et al., *J. Am. Chem. Soc.*, 105, 3101–3110 (1983), which discloses the use as a hydroxylation agent of such compounds as peroxovanadium oxypicolinate dihydrate, a chelate with picolinic acid (i.e., pyridine-2-carboxylic acid). This complex is prepared by the reaction of vanadium pentoxide with picolinic acid and aqueous hydrogen peroxide solution.

The hydroxylation reaction as disclosed in this and other papers apparently involves transfer of a peroxy moiety from the vanadium as an oxidant, and thus requires on the order of an equimolar amount of vanadium complex with respect to aromatic compound being oxidized. In order to be commercially feasible, a simple and effective method for regeneration of the vanadium compound would be required, thus effectively making the reaction catalytic with respect to vanadium.

A principal problem with the regeneration of the catalyst is that vanadium compounds are much more efficient at decomposing peroxide than at hydroxylating aromatic compounds. Thus, attempts at synthesis of the vanadium peroxo complex by simple addition of peroxide to the other reactants, including at least one vanadium compound, are unsuccessful since the peroxide formed is immediately decomposed by the vanadium compound rather than reacting therewith to form the peroxo complex. Various methods for overcoming this problem have been proposed, including phase transfer systems, the use of polymeric supports and slow or multiple additions of peroxide. None of these, however, has succeeded in producing a vanadium-containing promoter which is effective over a relatively long period in producing a hydroxylation product at a reasonable rate and with a reasonable degree of efficiency.

It is known that hydrogen peroxide can be produced by oxidation of hydroquinone homologs such as anthrahydroquinone. Reference is made, for example, to Heydorn et al., *CEH Product Review—Hydrogen Peroxide*, SRI International, pp. 741.5000H-M (August 1996). However, this method is expensive by reason of the cost of anthraquinone compounds, and any applicability of such reactions to the hydroxylation of aromatic compounds has apparently not been disclosed.

SUMMARY OF THE INVENTION

The present invention is based on the discovery of a method by which hydroquinones may be employed as agents for effective generation of peroxide species and their formal transfer to vanadium complexes, whereupon such complexes become active as hydroxylation reagents for aromatic compounds. The active vanadium species may be continuously regenerated, resulting in relatively high turnover of hydroxyaromatic compounds as products.

The invention, accordingly, is a method for converting an aromatic compound to a hydroxyaromatic compound which comprises contacting said aromatic compound with molecular oxygen in the presence of a vanadium compound and hydroquinone or a substituted hydroquinone.

DETAILED DESCRIPTION; PREFERRED EMBODIMENTS

The aromatic compounds which may be hydroxylated by the method of this invention include aromatic hydrocarbons such as benzene and substituted derivatives of such hydrocarbons. The preferred substituents are alkyl groups, although the use of aromatic compounds with other substituents such as halogen is also contemplated. Illustrative substituted aromatic hydrocarbons are toluene, the xylenes and the trimethylbenzenes.

Molecular oxygen may be employed as pure oxygen or as mixtures containing oxygen. Preferred mixtures for many purposes are those comprising principally nitrogen and oxygen, including air and "enriched air" typically comprising 28% oxygen and about 72% nitrogen. In general, nitrogen-oxygen mixtures containing about 15–40% oxygen by weight are particularly suitable.

As a promoter, any vanadium compound known to be convertible by peroxidation to a hydroxylation reagent may be employed. For the most part, the preferred compounds are complexes of pentavalent vanadium. Especially preferred are vanadium oxy chelates with such activating ligands as picolinic acid and substituted derivatives thereof such as 4-chloropicolinic acid.

It is within the scope of the invention to produce the promoter in situ by reaction of the activating ligand with a precursor vanadium compound. The preferred precursor compounds are tetravalent and pentavalent vanadium oxy salts with organic anions, especially alkoxides and β-diketone anions such as that derived from 2,4-pentanedione.

The hydroquinone compounds which may be employed according to the invention include unsubstituted hydroquinone (i.e., p-dihydroxybenzene) and substituted derivatives thereof. Typical substituents are alkyl and halide groups, and one or more of such substituents may be present. Illustrative substituted hydroquinones are methylhydroquinone, t-butylhydroquinone, chlorohydroquinone and tetrafluorohydroquinone.

A solvent is also preferably employed in the method of the invention. Preferred solvents include polar aprotic solvents such as acetonitrile, dimethyl sulfoxide and N-methylpyrrolidone, with acetonitrile often being preferred by reason of its effectiveness and relatively low cost. Reaction temperatures are not critical; temperatures in the range of about 30–120° C. are often beneficial.

The proportion of vanadium compound employed is not critical. It is typically in the range of about 10–7,500 ppm (parts per million) by weight based on aromatic compound. Proportions in the range of about 10–50 ppm frequently afford excellent turnover as defined hereinafter.

If the vanadium promoter is prepared in situ, the weight ratio of activating ligand to vanadium precursor is most often in the range of about 0.8–5.0:1, preferably about 1.5–3.0:1. Weight ratios of hydroquinone compound to vanadium compound are generally in the range of about 40–1,000:1.

The method of the invention may be performed by simply mixing the non-gaseous materials and pressurizing with the oxygen-containing gas, typically to a pressure in the range of about 2–5 MPa (megapascals). It is within the scope of the invention to introduce all the hydroquinone compound at the beginning of the reaction or to introduce it gradually during the reaction, for example via a high pressure pump. The hydroxylated products may be recovered by conventional methods including such art-recognized recovery operations as distillation, fractional crystallization and chromatographic separation.

The invention is illustrated by the following examples. All percentages are by weight. Various compounds used in the examples are identified as follows:

VPD—vanadium(IV) oxybis(2,4-pentanedionate),
VPR—vanadium(V) oxytris(isopropoxide),
PIC—picolinic acid,
CPIC—4-chloropicolinic acid,
BZ—benzene,
TL—toluene,
OX—o-xylene,
MX—m-xylene,
PX—p-xylene,
TMB—1,2,4-trimethylbenzene,
HQ—hydroquinone,
CHQ—chlorohydroquinone,
FHQ—perfluorohydroquinone,
MHQ—methylhydroquinone,
BHQ—t-butylhydroquinone.

EXAMPLES 1–5

A stainless steel autoclave was charged with 20 ml (17.6 g) of benzene, 40 ml of acetonitrile and various proportions of VPD, PIC and various hydroquinones. The autoclave was pressurized to 3.45 MPa with a mixture of 28% oxygen and 72% nitrogen and maintained at a temperature of 60° C. while hydroxylation occurred. When the reaction was complete as shown by cessation of oxygen uptake, the autoclave was cooled and opened and the mixture was analyzed.

The results are given in Table I. "Turnover" is the ratio of moles of hydroxylated product to gram-atoms of vanadium at the time of completion of the reaction.

TABLE I

|  | 1 | 2 | 3 | 4 | 5 |
|---|---|---|---|---|---|
| VPD, mg | 100 | 100 | 110 | 110 | 110 |
| PIC, mg | 450 | 55 | 100 | 110 | 90 |
| Hydroquinone: | | | | | |
| Identity | HQ | CHQ | FHQ | BHQ | MHQ |
| Weight | 10.00 | 13.16 | 4.90 | 15.45 | 12.80 |
| Phenol formed, mg | 1,610 | 280 | 840 | 713 | 208 |
| Turnover | 45 | 7.8 | 21.5 | 15.3 | 4.9 |

EXAMPLES 6–8

The autoclave of Examples 1–5 was charged with benzene, acetonitrile, vanadium compound and activating ligand and pressured to 2.45 MPa with the oxygen-nitrogen mixture. Hydroquinone (unsubstituted) was added slowly, using a high pressure pump. As shown by experience, reaction was essentially instantaneous upon hydroquinone addition; when it was complete, the mixtures were analyzed and the results are given in Table II.

TABLE II

|  | 6 | 7 | 8 |
|---|---|---|---|
| Benzene, g | 17.6 | 17.6 | 44.0 |
| Acetonitrile, ml | 65 | 50 | 61 |
| Vanadium compound: | | | |
| Identity | VPD | VIP | VPD |
| Weight, mg | 100 | 70 | 1.2 |
| Activating ligand: | | | |
| Identity | PIC | CPIC | PIC |
| Weight, mg | 200 | 970 | 2.3 |
| Hydroquinone, g | 0.50 | 15.45 | 2.00 |
| Phenol formed, mg | 150 | 580 | 170 |
| Turnover | 4.1 | 21.5 | 400 |

While a turnover greater than 1 was obtained in each example, it is apparent that Example 8, in which only 27 ppm of vanadium compound were employed relative to benzene, afforded the highest turnover.

EXAMPLES 9–11

The procedure of Examples 6–8 was repeated, substituting toluene for the benzene and employing unsubstituted hydroquinone, VPD and various picolinic acids. The results are given in Table III. In each example, the weight ratio of o-, m- and p-cresol obtained was 48:20:32.

TABLE III

|  | 9 | 10 | 11 |
|---|---|---|---|
| Toluene, g | 34.6 | 43.3 | 44.2 |
| Acetonitrile, ml | 20 | 31 | 31 |
| VPD, mg | 100 | 1.5 | 1.2 |
| Activating ligand: | | | |
| Identity | PIC | PIC | CPIC |
| Weight, mg | 179 | 2.5 | 2.2 |
| Hydroquinone, g | 10.00 | 0.74 | 0.56 |
| Cresol formed, mg | 635 | 250 | 88 |
| Turnover | 31.2 | 410 | 180 |

The particularly high turnover values in Examples 10 and 11, where the amounts of vanadium compound were 35 and 27 ppm respectively, is apparent.

EXAMPLES 12–16

The procedure of Examples 6–8 was repeated, substituting various xylene and trimethylbenzene compounds for the benzene and employing VPD, picolinic acid, unsubstituted hydroquinone and 25 ml of acetonitrile as solvent. The results are given in Table IV.

TABLE IV

|  | 12 | 13 | 14 | 15 | 16 |
|---|---|---|---|---|---|
| Hydrocarbon: | | | | | |
| Identity | PX | PX | MX | OX | TMB |
| Weight, g | 43.1 | 43.1 | 43.4 | 44.0 | 43.8 |

TABLE IV-continued

|  | 12 | 13 | 14 | 15 | 16 |
|---|---|---|---|---|---|
| VPD, mg | 100 | 100 | 100 | 100 | 101 |
| PIC, mg | 200 | 200 | 200 | 200 | 201 |
| Hydroquinone, mg | 550 | 970 | 1,170 | 1,040 | 1,020 |
| Product turnovers: |  |  |  |  |  |
| 2,5-Xylenol | 48 | 104 | — | — | — |
| 2,4-Xylenol | — | — | 115 | — | — |
| 2,6-Xylenol | — | — | 30 | — | — |
| 3,5-Xylenol | — | — | 9 | — | — |
| 2,3-Xylenol | — | — | — | 24 | — |
| 3,4-Xylenol | — | — | — | 43 | — |
| 2,3,5-Trimethylphenol | — | — | — | — | 30 |

What is claimed is:

1. A method for converting an aromatic compound to a hydroxyaromatic compound which comprises contacting said aromatic compound with molecular oxygen in the presence of a vanadium compound and hydroquinone or an alkyl- or halogen-substituted hydroquinone, wherein said aromatic compound is capable of conversion to the hydroxyaromatic compound with a turnover greater than 1 in the presence of said vanadium compound, where turnover is a ratio of moles of hydroxyaromatic compound to gram-atoms of vanadium at a time of completion of a reaction, and wherein said vanadium compound is capable of conversion to a hydroxylation reagent in the presence of molecular oxygen and hydroquinone or the alkyl- or halogen-substituted hydroquinone.

2. A method according to claim 1 wherein the molecular oxygen is in the form of a mixture comprising principally nitrogen and oxygen and containing about 15–40% oxygen by weight.

3. A method according to claim 2 wherein the vanadium compound is an oxy complex of pentavalent vanadium with an activating ligand.

4. A method according to claim 3 wherein the activating ligand is picolinic acid or a substituted picolinic acid.

5. A method according to claim 3 wherein the vanadium compound is produced in situ by reaction of the activating ligand with a precursor tetravalent or pentavalent vanadium compound.

6. A method according to claim 5 wherein the precursor vanadium compound is a 2,4-pentanedionate or an alkoxide.

7. A method according to claim 3 wherein the hydroquinone is an alkyl- or halogen-substituted hydroquinone.

8. A method according to claim 3 wherein the hydroquinone is unsubstituted.

9. A method according to claim 3 wherein a solvent is also present.

10. A method according to claim 9 wherein the solvent is a polar aprotic solvent.

11. A method according to claim 10 wherein the solvent is acetonitrile.

12. A method according to claim 3 wherein the reaction temperature is in the range of about 30–120° C.

13. A method according to claim 3 wherein the aromatic compound is benzene.

14. A method according to claim 3 wherein the aromatic compound is toluene.

15. A method according to claim 3 wherein the aromatic compound is xylene.

16. A method according to claim 3 wherein the aromatic compound is trimethylbenzene.

17. A method according to claim 3 wherein the proportion of vanadium compound is in the range of about 10–7,500 ppm by weight based on aromatic compound.

18. A method according to claim 17 wherein the proportion of vanadium compound is about 10–50 ppm by weight based on aromatic compound.

19. A method according to claim 3 wherein the pressure is in the range of about 2–5 MPa.

20. A method according to claim 19 wherein the weight ratio of hydroquinone or substituted hydroquinone to vanadium compound is in the range of about 40–1,000:1.

21. A method for converting an aromatic compound to a hydroxyaromatic compound which comprises contacting said aromatic compound with molecular oxygen in the presence of a vanadium compound and hydroquinone or an alkyl- or halogen-substituted hydroquinone, wherein said aromatic compound is capable of conversion to the hydroxyaromatic compound with a turnover greater than 1 in the presence of said vanadium compound, where turnover is a ratio of moles of hydroxyaromatic compound to gram-atoms of vanadium at a time of completion of a reaction, wherein said vanadium compound is present at a level of about 10 to about 7,500 ppm based on the aromatic compound and said vanadium compound is capable of conversion to a hydroxylation reagent in the presence of molecular oxygen and hydroquinone or the alkyl- or halogen-substituted hydroquinone, and wherein a weight ratio of said hydroquinone or the alkyl- or halogen-substituted hydroquinone to the vanadium compound is in a range of about 40:1 to about 1000:1.

22. A method for converting an aromatic compound to a hydroxyaromatic compound which comprises contacting said aromatic compound with molecular oxygen in the presence of a vanadium compound and hydroquinone or an alkyl- or halogen-substituted hydroquinone in a polar aprotic solvent under a pressure of about 2 MPa to about 5 MPa at a temperature of about 30° C. to about 120° C., wherein said aromatic compound is capable of conversion to the hydroxyaromatic compound with a turnover greater than 1 in the presence of said vanadium compound, where turnover is a ratio of moles of hydroxyaromatic compound to gram-atoms of vanadium at a time of completion of a reaction, wherein said vanadium compound is present at a level of about 10 to about 7,500 ppm based on the aromatic compound and said vanadium compound is capable of conversion to a hydroxylation reagent in the presence of molecular oxygen and hydroquinone or the alkyl- or halogen-substituted hydroquinone, and wherein a weight ratio of said hydroquinone or the alkyl- or halogen-substituted hydroquinone to the vanadium compound is in a range of about 40:1 to about 1000:1.

* * * * *